US012661425B1

(12) United States Patent
Watkins

(10) Patent No.: US 12,661,425 B1
(45) Date of Patent: Jun. 23, 2026

(54) AROMA GENERATING AND DISPENSING MEANS

(71) Applicant: John F. Watkins, Cleveland, OH (US)

(72) Inventor: John F. Watkins, Cleveland, OH (US)

( * ) Notice: Subject to any disclaimer, the term of this patent is extended or adjusted under 35 U.S.C. 154(b) by 573 days.

(21) Appl. No.: 18/098,863

(22) Filed: Jan. 19, 2023

Related U.S. Application Data

(60) Provisional application No. 63/300,716, filed on Jan. 19, 2022.

(51) Int. Cl.
A61L 9/12 (2006.01)

(52) U.S. Cl.
CPC .......... A61L 9/125 (2013.01); A61L 2209/111 (2013.01); A61L 2209/134 (2013.01)

(58) Field of Classification Search
CPC ....................................................... A61L 9/125
See application file for complete search history.

(56) References Cited

U.S. PATENT DOCUMENTS

| | | | |
|---|---|---|---|
| 2,540,144 A | 2/1951 | Stern | |
| 2,813,452 A | 11/1957 | Laube | |
| 3,795,438 A | 3/1974 | Roslyng et al. | |
| 6,015,902 A | 1/2000 | Bieniarz et al. | |

| | | | |
|---|---|---|---|
| 6,239,857 B1 | 5/2001 | Wittek | |
| 8,747,735 B2 | 6/2014 | Homer | |
| 9,445,040 B2 | 9/2016 | Watson | |
| 10,010,640 B1 * | 7/2018 | Li | F21S 9/02 |

FOREIGN PATENT DOCUMENTS

| | | | | |
|---|---|---|---|---|
| JP | 2009512474 A | * | 3/2009 | A61L 9/037 |

OTHER PUBLICATIONS

English translation of JP2009512474-A (Year: 2009).*

* cited by examiner

*Primary Examiner* — Sean E Conley
(74) *Attorney, Agent, or Firm* — Cramer Patent & Design, PLLC.; Aaron R. Cramer

(57) ABSTRACT

An aroma generating and dispensing means is a device which produces olfactory effects while watching television shows. The device is housed in an enclosure that is approximately twelve inches (12") deep, six inches (6") wide and six inches (6") tall. A power supply is located inside which energizes a control circuit and voice recognition hardware and associated software. The software is programmed to recognize various keywords such as cooking ingredients that would be verbally reproduced by the audio associated with a cooking program. The circuitry would then energize various corresponding vaping modules contained within the enclosure that are pre-loaded with different liquid fragrances. A vacuum pump then distributes these scents outside of the enclosure and into a nasal cannula so that they can be enjoyed by occupants within the room. When depleted, the various modules can be reloaded by the user.

5 Claims, 5 Drawing Sheets

AROMA GENERATING AND DISPENSING MEANS

RELATED APPLICATIONS

The present invention was first described in and is a continuation of U.S. Provisional Patent Application No. 63/300,716 filed on Jan. 19, 2022, the entire disclosures of which are incorporated herein by reference.

FIELD OF THE INVENTION

The present invention relates generally to an aroma generating dispenser and more specifically to an aroma generating and dispensing means that acts in concert with an electronic device such as a television set.

BACKGROUND OF THE INVENTION

Television sets have become a common electronic entertainment device in many homes and are used to watch a wide range of programming, from news and drama to education and live entertainment. They engage the sense of sight with high-definition screens and the sense of sound with realistic multiple channel sound systems. However, one sense that has not been utilized in television viewing is the sense of smell. In the past, attempts have been made to incorporate this sense into television viewing, but they have not been successful. With the advent of new technologies such as voice recognition software and vaping modules, it is now possible to effectively incorporate the sense of smell into television viewing.

The aroma generating and dispensing means provides an opportunity to experience olfactory senses associated with watching cooking programs in a quick, easy, and effective manner. The device can be used to dispense various aromas, such as the smell of food, to enhance the viewing experience. This can make watching cooking programs more enjoyable and interactive as it simulates the experience of actually cooking and smelling the food.

Additionally, it can also be used in other types of programming such as nature documentaries to provide a more immersive experience. Overall, the use of the aroma generating, and dispensing means can enhance the overall television viewing experience by engaging one more sense.

SUMMARY OF THE INVENTION

The aroma generating and dispensing means is a device that has a generator/dispenser unit that receives an input and translates it to an aroma, a housing containing various components such as electrical components, reservoirs, and microprocessors, and an output that allows the aroma to be released into the external environment. The input may be received in several ways, such as via audible sound, wireless communication, or broadcast sound. The wireless communication can be through Bluetooth® technology with a voice recognition module. The input received may be translated into an aroma and dispensed to the external environment, and the content can resemble squeezing a lemon which would induce dispensing of the aroma that smells like the lemon.

Upon receipt of the input, the voice recognition module may record and transmit the sound to a relay control module and relay control board, which then communicates with the system to produce the aroma. The aroma may then be placed in fluid communication with a vapor coil which is activated by the relay control board, vaporizing the aroma. A vacuum pump may be activated by the relay control board and is in fluid communication with the vapor coil, assisting in dispensing the aroma through the output to the external environment, in a concentration capable of being sensed by the user. The voice recognition module may also be able to pick-up audible sound from wireless communication and receive broadcast sound regarding the content of visual display via the microphone. The device may also have a power cord that provides electrical communication to the housing from a power source, which has a transformer in the electrical communication with the power source providing power.

BRIEF DESCRIPTION OF THE DRAWINGS

The advantages and features of the present invention will become better understood with reference to the following more detailed description and claims taken in conjunction with the accompanying drawings, in which like elements are identified with like symbols, and in which:

DESCRIPTIVE KEY

Figure 1:
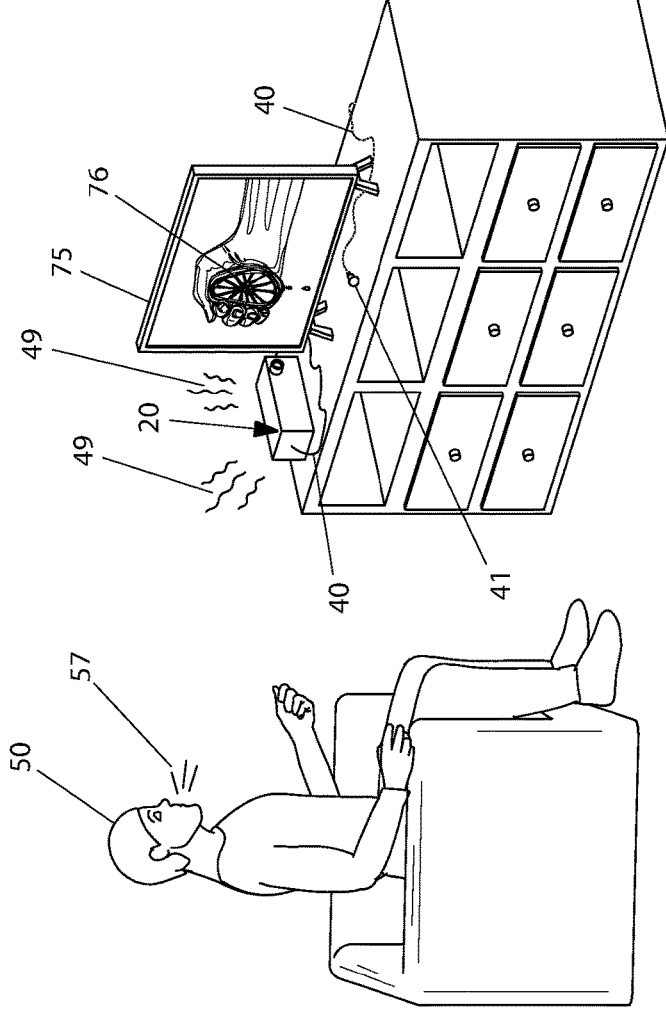
FIG. 1 is an environmental perspective view of an aroma generating and dispensing means being utilized by a user and alternately via electrical communication with a visual display, according to a preferred embodiment of the present invention.
Figure 1:

10 aroma generating and dispensing means
15 power cord
20 generator/dispenser unit
21 housing
22 port
30 outlet
40 cable
41 microphone
42 voice recognition module
43 relay control module
44 relay board
45 vapor coil
46 vacuum pump
47 transformer
49 aroma
49*a* alternate aroma
49*b* another alternate aroma
49*c* yet another alternate aroma
50 user
57 audible sound
75 visual display
76 content

76a alternate content
76b another alternate content
76c yet another alternate content

DESCRIPTION OF THE INVENTION

The best mode for carrying out the invention is presented in terms of its preferred embodiment, herein depicted within FIGS. 1 through 5. However, the invention is not limited to the described embodiment, and a person skilled in the art will appreciate that many other embodiments of the invention are possible without deviating from the basic concept of the invention and that any such work around will also fall under scope of this invention. It is envisioned that other styles and configurations of the present invention can be easily incorporated into the teachings of the present invention, and only one (1) particular configuration shall be shown and described for purposes of clarity and disclosure and not by way of limitation of scope. All of the implementations described below are exemplary implementations provided to enable persons skilled in the art to make or use the embodiments of the disclosure and are not intended to limit the scope of the disclosure, which is defined by the claims.

The terms "a" and "an" herein do not denote a limitation of quantity, but rather denote the presence of at least one (1) of the referenced items.

Referring now to FIG. 1, there is illustrated an aroma generating and dispensing means 10 that includes a generator/dispenser unit 20 that is selectively capable of receiving an input and translating that to an aroma 49 in at least two (2) ways. A first way is to receive an input received via an audible sound 57 or by wireless communication with a voice recognition module 42. A second way is to receive broadcast sound regarding content 76, 76a, 76b, 76c from a visual display 75 and conducted over a microphone 41 and a cable 40. Either first way or second way results in translating the audible sound 57 or content 76 to a system to produce an aroma 49, 49a, 49b, 49c and dispensing the aroma 49, 49a, 49b, 49c to the environment. In the exemplary embodiment, the content 76 resembles squeezing a lemon which would induce the dispensing of an aroma 49 that smells like lemon.

Figure 2:
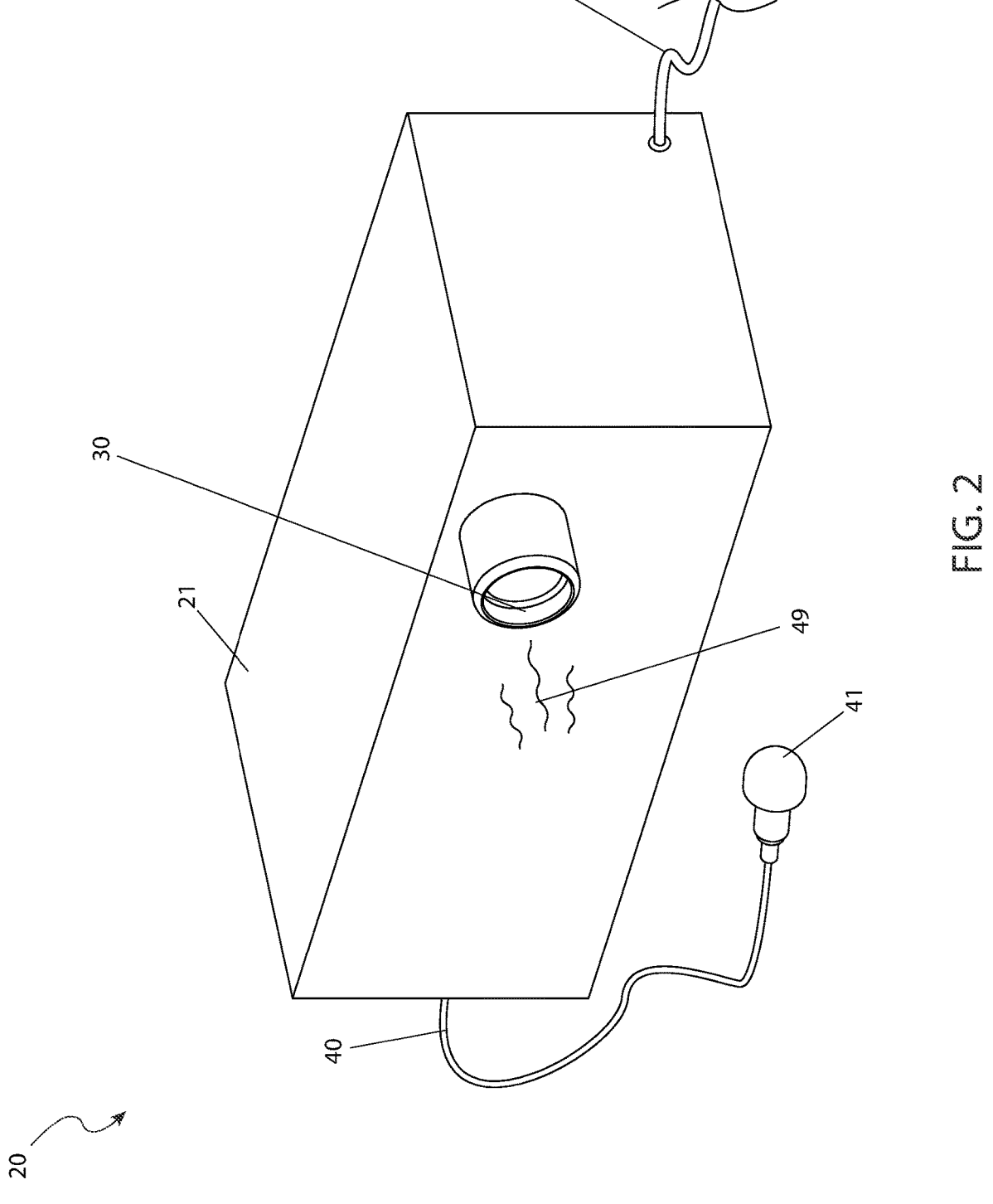
FIG. 2 is a perspective view of a generator/dispenser portion of the aroma generating and dispensing means, according to the preferred embodiment of the present invention.
Figure 3A:
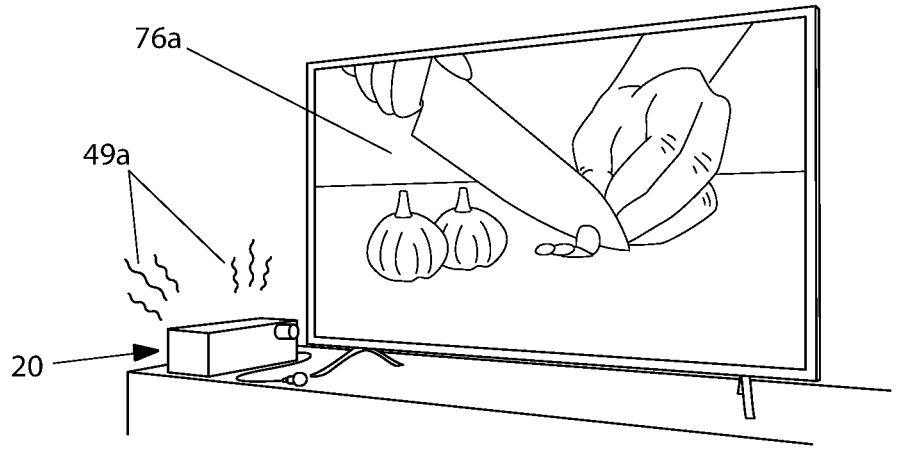
FIG. 3*a* is a view of an alternate content.
Figure 3B:
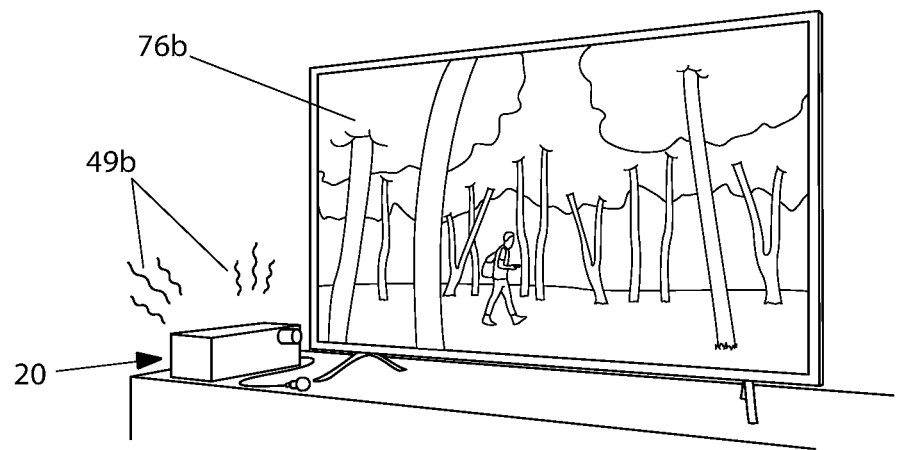
FIG. 3*b* is a view of another alternate content.
Figure 3C:
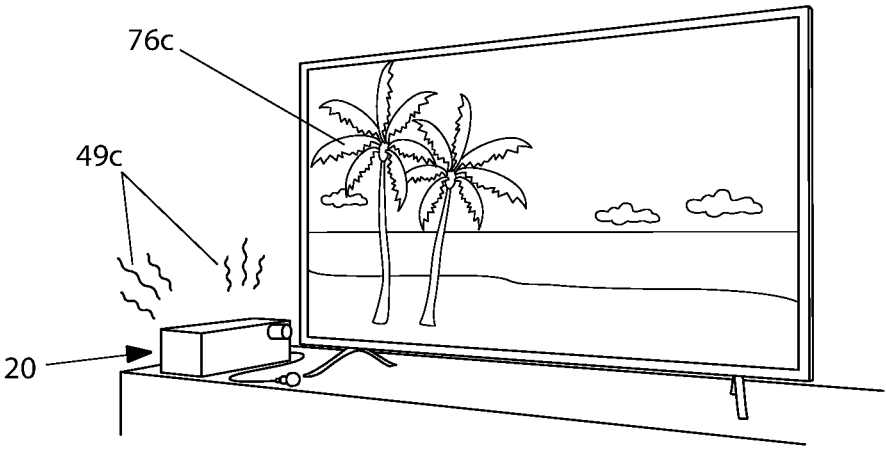
FIG. 3*c* is a view of yet another alternate content.

FIG. 2 illustrates a housing 21 of the generator/dispenser unit 20. The housing 21 is configured to house all electrical components, a dispensing mechanism, any reservoirs, wired or wireless communication components, microprocessors, or any other modes of producing and dispensing an aroma 49m 49a, 49b, 49c upon receipt of an audible sound 57 from a user 50 or broadcast sound regarding content 76, 76a, 76b, 76c from a visual display 75. An output 30 is located on the outer surface of the housing 21 that is in environmental communication between the aroma producing features within the housing 21 and the environment upon the type of input (i.e., the voice recognition module 42 picking up an audible sound 57 from a user 50 or wireless communication, or by receiving a broadcast sound regarding the content 76, 76a, 76b, 76c of a visual display 75 via the microphone 41) as indicated in the textual indicia. The input is thusly transferred to the modes of producing and dispensing an aroma 49, 49a, 49b, 49c housed within the housing 21. A power cord 15 is present to provide electrical communication to the inner working features of the housing 21 from a power source.

Figure 4:
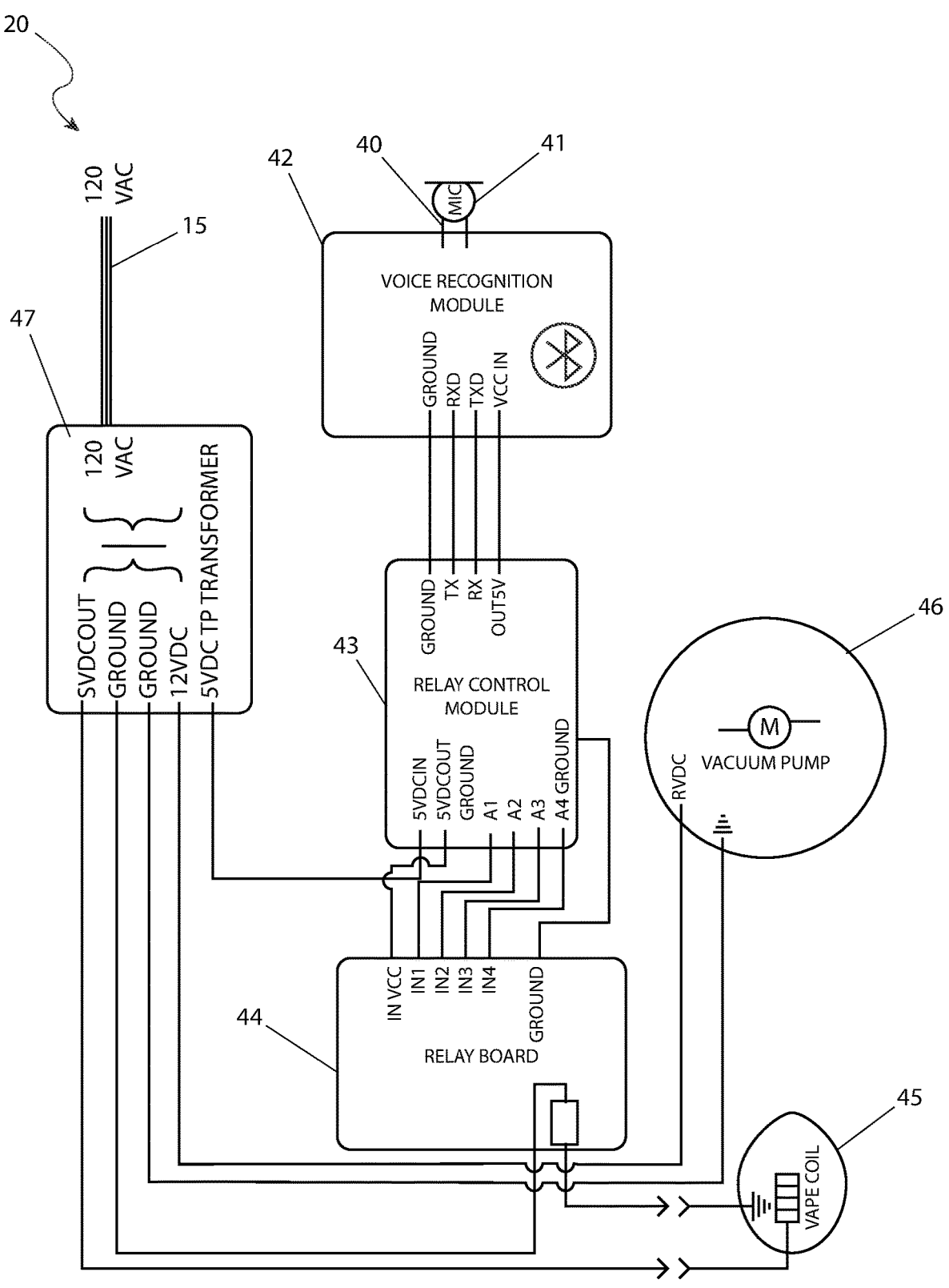
FIG. 4 is an electrical schematic of the generator/dispenser, according to the preferred embodiment of the present invention.
Figure 5:
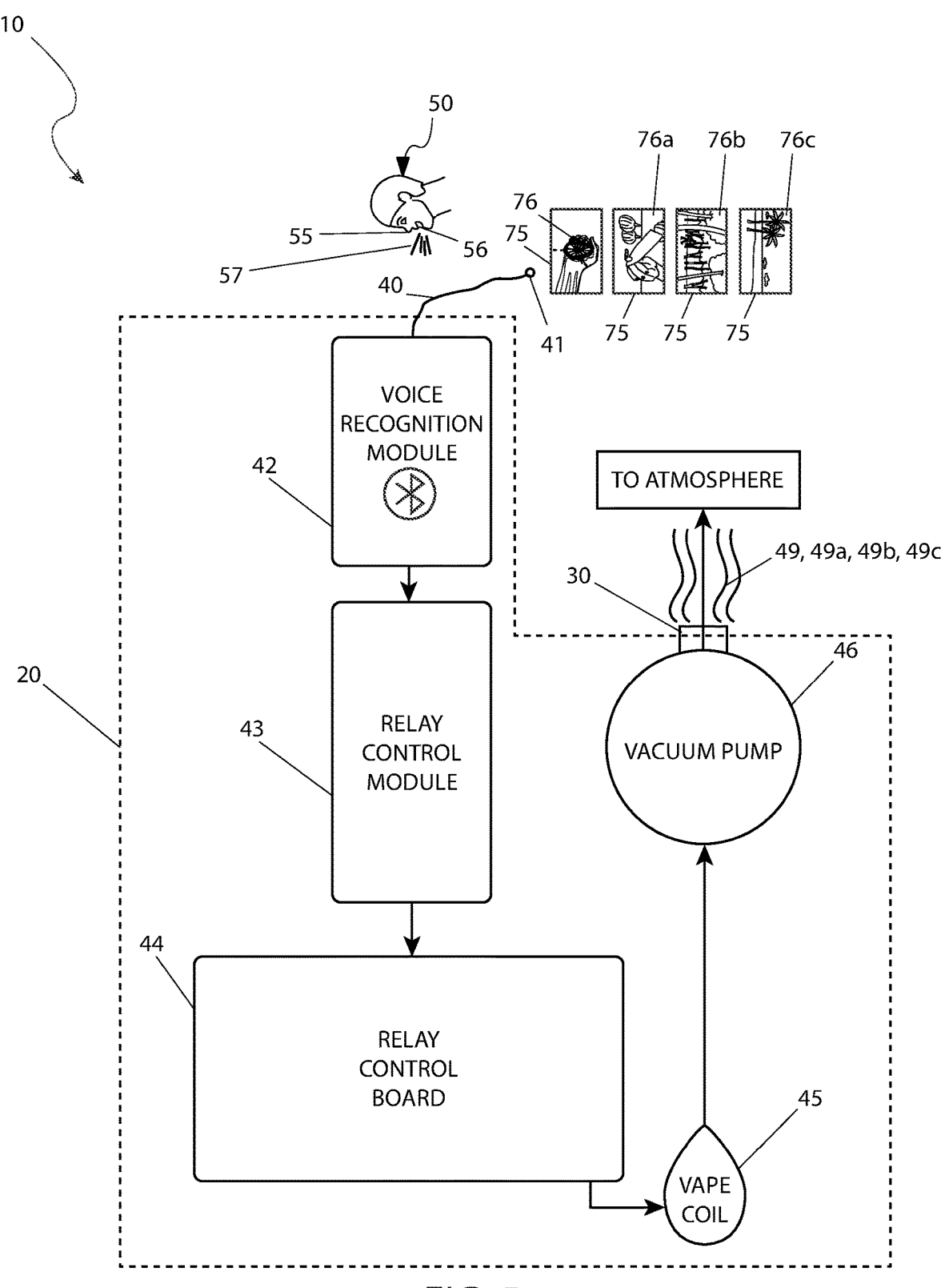
FIG. 5 is an environmental pictorial representation of the aroma generating and dispensing means, according to the preferred embodiment of the present invention.

FIGS. 4 and 5 depict an electrical schematic and a pictorial representation of a method of use of the aroma generating and dispensing means 10. Upon receipt of the input (i.e., the voice recognition module 42 picking up an audible sound 57 from a user 50 or wireless communication, or by receiving a broadcast sound regarding the content 76, 76a, 76b, 76c of a visual display 75 via the microphone 41), a voice recognition module 42 records and transmits a sensed sound to a relay control module 43 and a relay control board 44 to determine if a sensed sound will prompt a recipe for an aroma 49, 49a, 49b, 49c that is capable of being produced with ingredients located in said housing 21. If so, the relay control board 44 communicates this to produce the desired aroma 49, 49a, 49b, 49c, which is then placed in fluid communication with a vapor coil 45, which is activated by the relay control board 44. The vapor coil 45 will vaporize the aroma 49, 49a, 49b, 49c. A vacuum pump 46, also activated by the relay control board 44, is in fluid communication with the vapor coil 45. The vacuum pump 46 assists in dispensing the aroma 49, 49a, 49b, 49c through the output 30 to the environment, which is produced in a concentration capable of being sensed by the user 50. A transformer 47 is present to be in electrical communication with a power source provided power.

As is seen in FIG. 5, the first way of inputting is when an audible sound 57 emanates from a user 50 or is transmitted by wireless communication protocols such as Bluetooth™ to the voice recognition module 42. The second way of inputting is by receiving broadcast sound regarding content 76, 76a, 76b, 76c that is shown and heard from a visual display 75 and transmitted to the voice recognition module 42 via the microphone 41 and cable 40. By way of an example, if a cooking show on the visual display 75 produces content 76a associated with the word "garlic" (as in FIG. 3a), produces content 76b associated with the word "pine" (as in FIG. 3b) or produces content 76c associated with the word "beach/ocean/sea" (as in FIG. 3c) and broadcasts sound that invokes that word, a generator/dispenser unit 20 that incorporates the ingredient or ingredients to produce an aroma 49, 49a, 49b, 49c will be able to be produce, vaporize, and dispense the selected aroma 49, 49a, 49b, 49c. It is assumed that functional equivalents of the word that is inputted may be programmed to provide the same dispensation of the selected aroma 49, 49a, 49b, 49c.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated.

The invention claimed is:

1. An aroma generating and dispensing device, comprising:
   a housing;
   at least one reservoir disposed within the housing and containing an aroma material;
   a voice recognition module disposed within the housing and configured to receive an audible sound from a user;
   a relay control module disposed within the housing and in electrical communication with the voice recognition module;
   a relay control board disposed within the housing and in electrical communication with the relay control module;
   a vapor coil disposed within the housing and positioned in fluid communication with the at least one reservoir;

a vacuum pump disposed within the housing and positioned in fluid communication with the vapor coil;

an output port disposed on an outer surface of the housing and in fluid communication with the vacuum pump; and, a power cord in electrical communication with internal electrical components of the housing;

wherein:

the voice recognition module transmits a sensed audible sound to the relay control module;

the relay control module communicates the sensed audible sound to the relay control board;

the relay control board activates the vapor coil to vaporize the aroma material; and, the relay control board activates the vacuum pump to draw vaporized aroma from the vapor coil and expel the vaporized aroma through the output port into an external environment.

2. The device of claim 1, wherein the vacuum pump dispenses the vaporized aroma in a concentration capable of being sensed by the user.

3. The device of claim 1, further comprising a microphone in electrical communication with the voice recognition module.

4. The device of claim 1, wherein the audible sound corresponds to content associated with a visual display.

5. The device of claim 1, further comprising a transformer disposed within the housing and positioned between the power cord and the relay control board.

* * * * *